(12) United States Patent
Galkin

(10) Patent No.: US 7,248,668 B2
(45) Date of Patent: Jul. 24, 2007

(54) MAMMOGRAPHY COMPRESSION DEVICES AND METHODS

(76) Inventor: Benjamin M. Galkin, 35 Ivy La., Cherry Hill, NJ (US) 08002

( * ) Notice: Subject to any disclaimer, the term of this patent is extended or adjusted under 35 U.S.C. 154(b) by 0 days.

(21) Appl. No.: 11/279,280

(22) Filed: Apr. 11, 2006

(65) Prior Publication Data

US 2006/0165215 A1  Jul. 27, 2006

(51) Int. Cl.
*A61B 6/04* (2006.01)
(52) U.S. Cl. .................................................... 378/37
(58) Field of Classification Search ................ 378/37, 378/162–165, 167, 177; 128/915
See application file for complete search history.

(56) References Cited

U.S. PATENT DOCUMENTS

| | | | | |
|---|---|---|---|---|
| 4,962,515 | A | 10/1990 | Kopans | 378/37 |
| 5,199,056 | A | 3/1993 | Darrah | 378/37 |
| 5,412,706 | A * | 5/1995 | Deibel | 378/162 |
| 5,479,927 | A | 1/1996 | Shmulewitz | 128/660.09 |
| 5,506,877 | A | 4/1996 | Niklason et al. | 378/37 |
| 5,706,327 | A | 1/1998 | Adamkowski et al. | 378/37 |
| 6,049,583 | A | 4/2000 | Galkin | 378/37 |
| 6,577,702 | B1 | 6/2003 | Lebovic et al. | 378/37 |
| 6,765,984 | B2 | 7/2004 | Higgins et al. | 378/37 |
| 6,850,590 | B2 | 2/2005 | Galkin | 378/37 |
| 6,968,033 | B2 | 11/2005 | Lebovic et al. | 378/37 |
| 6,969,033 | B2 | 11/2005 | Van der Linden | 248/177.1 |
| 6,974,255 | B1 | 12/2005 | Hixson, Sr. | 378/208 |
| 6,975,701 | B2 | 12/2005 | Galkin | 378/37 |
| 2005/0207528 | A1 * | 9/2005 | Hjarn | 378/37 |
| 2006/0050844 | A1 | 3/2006 | Galkin | 378/37 |

OTHER PUBLICATIONS

Clark, D.J., et al., "Pressure Measurements During Automatic Breast Compression in Mammography", *J. Biomed Eng.*, 1990, 12(5), 444-446.
Saab, M.A. "Applications of High-Pressure Balloons in the Medical Device Industry", 1999, Advanced Polymers, Inc., http://www.advpoly.com/NewsData/BalloonPaper.pdf, 19 pages.

* cited by examiner

*Primary Examiner*—Jurie Yun
(74) *Attorney, Agent, or Firm*—Woodcock Washburn LLP

(57) ABSTRACT

Compression devices and mammography units using the same, and methods of using the same during imaging of a patient's breast are provided. The devices compress the breast against a bucky without the need for a traditional mammography unit compression paddle. The devices comprise at least one x-ray transparent inflatable chamber for containing a fluid, for example, a pressurized gas. In use, at least one surface of the chamber expands in the direction of the bucky. The devices secure the breast to the bucky by wrapping over the tube-side surface of the breast. Compressed air, for example, can be introduced, manually or automatically, to inflate the chamber. As the chamber expands, breast motion is limited and the breast is compressed against the surface of the bucky.

21 Claims, 3 Drawing Sheets

MAMMOGRAPHY COMPRESSION DEVICES AND METHODS

FIELD OF THE INVENTION

The present inventions relate to the field of radiology and particularly to mammography. More specifically, the present inventions relate to mammography compression devices and methods of use.

BACKGROUND OF THE INVENTION

Mammography is the process of obtaining x-ray images of the human breast for diagnosis or surgery. It involves positioning a patient's breast in a desired orientation against a cassette holder (also known as a "bucky") of a mammography unit, compressing the breast with a compression device (e.g., a compression paddle), and then exposing the breast to x-rays to create a latent image of the breast on an image receptor. After exposure, the compression device is released. An example of the image receptor is a film in contact with an intensifying screen contained within a cassette. The cassette is inserted into the cassette holder before every image is taken and removed after every image. The film is removed from the cassette and developed to produce a radiographic image of the breast. Another type of image receptor is a solid state device, and the image is obtained electronically.

A complete mammographic study usually involves at least two x-ray exposures of each breast. One exposure is a craniocaudal view in which the breast is compressed in a superior-inferior direction, i.e., from the direction of the patient's head downward, against a tube-side surface of the cassette holder. The plane of the tube-side surface of the cassette holder is parallel to the floor and the x-ray beam is directed vertically downward. A second exposure is a lateral or oblique view in which the breast is compressed mediolaterally, i.e., from the direction of the patient's midline sidewise, against the tube-side surface of the cassette holder which is angled, along with the axis of the x-ray beam, relative to the floor.

Typically, the compression device is a compression paddle, which includes a rectangular flat plate that is attached to the mammography unit between an x-ray tube assembly and the bucky. The edges of the paddle are usually turned upward away from the bucky to provide a smooth curved surface for patient comfort. The compression paddle is usually made of thin, light-transparent, plastic that absorbs only a small fraction of the incident x-ray beam. The compression paddle is moved either manually or by power drive to apply a compression force to the breast, thereby limiting breast motion and flattening the breast against the cassette holder to a near uniform thickness to improve image quality. U.S. Pat. No. 6,049,583 issued to the present inventor discusses methods and apparatus for measuring compression force in mammography. During compression, parts of the patient's body come into contact with the compression paddle. After x-ray exposure, the compression force is released for patient comfort.

As is well known in the field, to properly position the breast, the patient's chest wall or other regions of the body, depending on the desired view, are brought into tight contact with the rigid surfaces of the cassette holder, its edges, and corners. This procedure has the effect of forcing the patent's anatomy to contour to the shape of the cassette holder, which often causes patient discomfort and pain. Oftentimes, overlapping internal structures are present within the breast tissue that can obscure their delineation in a radiographic image. As a result, it is often necessary to reposition the breast slightly in order to arrive at a diagnosis. This requires repositioning the patient for each view with the attendant discomfort due in part to repeat compressions. U.S. Pat. No. 6,850,590 by the present inventor, incorporated herein by reference, discusses methods of reshaping the breast without repositioning.

It is well known that many women find the procedure for compressing the breast to be uncomfortable and for some, even painful. Methods to provide patient comfort during this procedure involve adding cushioning material to the patient contact surfaces of the compression paddle. Examples are described in U.S. Pat. Nos. 6,577,702 and 6,968,033 issued to Lebovic et al.; and U.S. Pat. No. 6,765,984 issued to Higgins, et al. Also, U.S. Pat. No. 6,975,701 and U.S. Patent Publication No. 20060050844 by the present inventor, each of which is incorporated herein by reference, describe cushioning devices for compression paddles. U.S. Pat. No. 5,479,927, issued to Shmulewitz discusses a gel pad attached to the patient-contact surface of the compression paddle.

To properly position the patient's breast in a desired orientation before exposure, a technologist is guided by a light beam originating from the x-ray tube assembly that passes through a collimator and the compression paddle to illuminate the area of the bucky that will be exposed to x-rays, i.e., the imaging area. Sometimes, adding cushioning materials to compression paddles blocks the light and impedes proper positioning of the breast.

Other attempts to resolve problems with the compression paddle have included redesigning the shape of the paddle or its angulation, e.g. U.S. Pat. Nos. 4,962,515; 5,199,056; 5,506,877; 5,706,327; 6,974,255.

There remains a great need for devices and methods to compress a patient's breast during mammography that can minimize or eliminate the pain and discomfort experienced by the patient. For example, there is a need for devices that limit motion of the breast without exerting excessive compression force. There exists a need in mammography for being able to compress a patent's breast without a paddle to reduce patient discomfort. There also exists a need for a compression device that operates with fluid, for example, air, pressure to compress the breast. There also exists a need for devices and methods that do not inhibit visible light from the mammography unit from being transmitted toward the patient's breast and bucky to facilitate proper positioning of a breast.

SUMMARY OF THE INVENTION

Compression devices for a mammography unit and methods of using the same during imaging of a patient's breast are provided. The devices compress the breast against a bucky without the need for a traditional mammography unit compression paddle. The devices comprise at least one x-ray transparent inflatable chamber for containing a fluid, for example, a pressurized gas. When fluid is introduced into the chamber, at least one surface of the chamber expands in the direction of the bucky. As the chamber expands, breast motion is limited and the breast is compressed against the surface of the bucky.

Mammography units are also provided, that comprise a bucky comprising an imaging area; a compression device comprising at least one x-ray transparent inflatable chamber and a manifold operatively associated with the inflatable chamber for introducing a fluid into the inflatable chamber and/or for receiving the fluid from the inflatable chamber; wherein when fluid is introduced into the at least one chamber of the compression device, at least one surface of the chamber expands in the direction of the bucky. In one embodiment, a source of compressed air that is in fluid communication with the manifold is provided.

Methods in accordance with the present invention comprise: securing a compression device comprising at least one inflatable chamber over a tube-side surface of the breast; inflating the at least one chamber of the compression device with a fluid; compressing the breast between the at least one inflatable chamber and an imaging area of a bucky; and transmitting x-rays through the breast and onto the mammogram. In one embodiment, the methods further comprise using a source of compressed air to inflate the at least one chamber of the compression device. In another embodiment, to avoid direct contact with the patient's skin, a disposable x-ray transparent thin plastic sheet can be used between the tube-side surface of the breast and the inflatable chamber.

BRIEF DESCRIPTION OF THE DRAWINGS

The present invention will be better understood, and its numerous objects and advantages will become apparent to those skilled in the art by reference to the following detailed description when taken in conjunction with the following drawings, in which.

DETAILED DESCRIPTION OF ILLUSTRATIVE EMBODIMENTS

Figure 1:
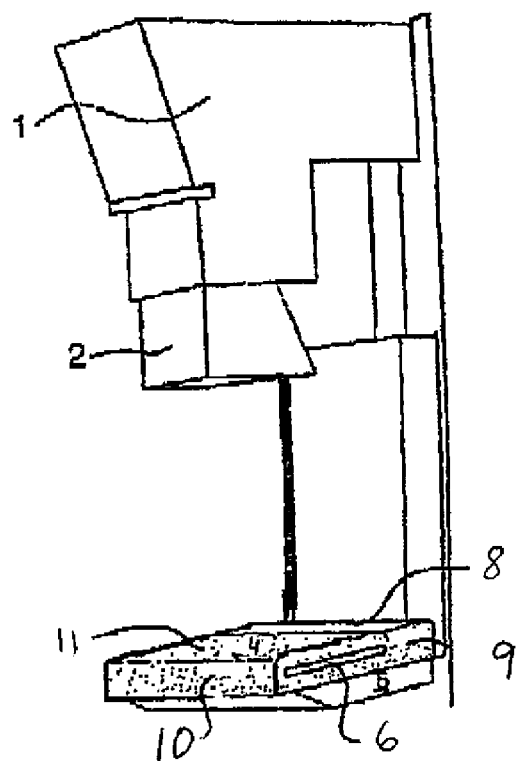
FIG. 1 is a schematic oblique view of a section of a mammography unit in accordance with the present invention.

Compression devices for a mammography unit and methods of using the same during imaging of a patient's breast are provided. The devices compress the breast against a bucky without the need for a traditional mammography unit compression paddle. The devices comprise at least one x-ray transparent inflatable chamber for containing a fluid, for example, a pressurized gas. Inflatable chambers are, for example, medically acceptable balloons. When fluid is introduced into the chamber, at least one surface of the chamber expands in the direction of the bucky. The devices secure the breast to the bucky by wrapping over the tube-side surface of the breast. Side flaps secure the device to and/or around the bucky. Generally, when in position over the breast (and not inflated), the inflatable chamber partially conforms to the shape of the breast. Compressed air, for example, can be introduced, manually or automatically, to inflate the chamber. As the chamber expands, breast motion is limited and the breast is compressed against the surface of the bucky.

Mammography units are also provided, that comprise a bucky comprising an imaging area; a compression device comprising at least one x-ray transparent inflatable chamber and a manifold operatively associated with the inflatable chamber for introducing a fluid into the inflatable chamber and/or for receiving the fluid from the inflatable chamber; wherein when fluid is introduced into the at least one chamber of the compression device, at least one surface of the chamber expands in the direction of the bucky. In one embodiment, a source of compressed air that is in fluid communication with the manifold is provided.

Inflatable chambers increase in volume when pressurized fluid is introduced. A medically acceptable balloon is an example of an inflatable chamber. Chambers used in embodiments of the present invention can be, for example, high pressure balloons. High pressure balloons are used in various applications in the medical industry, such as in angioplasty. See Saab, *Applications of High-Pressure Balloons in the Medical Device Industry*, http:// www.advpoly-.com/NewsData/BalloonPaper.pdf.

In some applications of the present invention, the device comprises multiple chambers. For example, a second inflatable chamber can be used to help distribute the compression force exerted against the breast. The shape of the chambers can vary as needed.

In some embodiments, there is an x-ray transparent cover that substantially surrounds the inflatable chamber. In some instances, it may be desirable that the x-ray transparent cover is compressible. In other instances, the x-ray transparent cover is disposable. A combination of compressible and disposable covers can also be used. For example, in one embodiment, a cuff made of compressible material can have a pocket for holding a high pressure balloon where the cuff wraps around the breast and the bucky. In another embodiment, to avoid direct contact with the patient's skin, a disposable x-ray transparent thin plastic sheet can be used between the tube-side surface of the breast and the inflatable chamber.

Any portion of the devices can comprise radiopaque indicia. For example, the indicia can impart information onto the mammogram in an area away from the breast.

Regarding indicia, it may be desirable to provide information including, but not limited to, the physical properties of the compression device, such as density or thickness, the location of the device, the manufacturer of the device, and/or the date of manufacture. In addition, it may be useful for compression devices to have unique serial numbers, that may, for example, aid in tracking re-use of the devices. In accordance with the present invention, information can be provided on the mammogram in an area away from an image of the breast.

Reference herein to "cassette holder" and "bucky" means the device that holds an image receptor for the creation of a mammogram, regardless of whether the image receptor is film-based or digital.

An identifier is radiopaque such that identifying indicia can be either x-ray transparent or radiopaque, and the remaining portion of the identifier would be radiopaque or x-ray transparent, respectively. By reference to the radiopaque nature of an identifier, it is understood that the identifier may not be completely radiopaque, but its radiopacity would be sufficiently different from the radiopacity of the surrounding materials, e.g., x-ray transparent compressible materials or x-ray transparent covers, so as to be recordable, e.g. radiographically, on a mammogram. The identifier can comprise a variety of radiopaque materials, e.g., paper, plastic, or metal. In such an embodiment, identifying indicia would be x-ray transparent. If desired, in another embodiment, identifying indicia can be imprinted with radiopaque ink onto x-ray transparent compressible material or x-ray transparent covers.

Methods in accordance with the present invention comprise: securing a compression device comprising at least one inflatable chamber over a tube-side surface of the breast; inflating the at least one chamber of the compression device with a fluid; compressing the breast between the at least one inflatable chamber and an imaging area of a bucky; and transmitting x-rays through the breast and onto the mammogram. In one embodiment, the methods further comprise using a source of compressed air to inflate the at least one chamber of the compression device.

Figure 2:
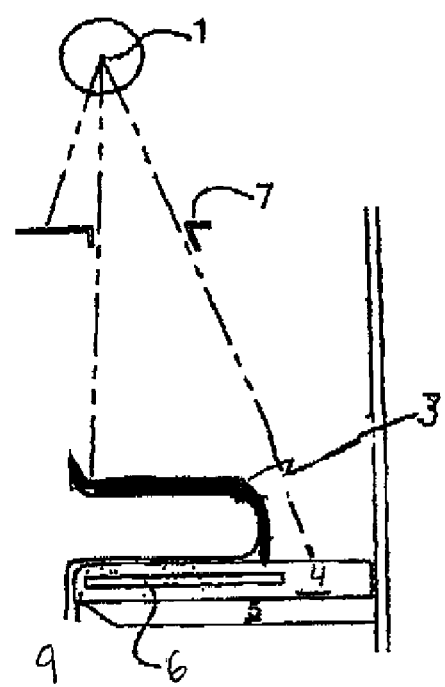
FIG. 2 is a schematic lateral view of FIG. 1 depicting a breast compressed with a compression device in accordance with the present invention.

Referring now to the drawings wherein reference numerals refer to like elements, FIGS. 1 and 2 depict two views of a mammography unit in accordance with an embodiment of the present invention having an x-ray tube 1 that produces an x-ray beam (not numbered) connected to a cone 2 that houses a collimator 7. The collimator 7 restricts the size and shape of the x-ray beam in any plane perpendicular to the axis of the x-ray beam. The x-ray beam also passes through a compression device 3 according to the present invention. A cassette holder 4, comprises a tube-side surface containing an imaging area 11 and a solid area 8; an outer surface 10 that is in close proximity or in contact with a patient's chest wall during examination; and a cassette tunnel opening 6. Generally, in a film-based cassette holder, a cassette tunnel located below the imaging area houses an antiscatter grid and a cassette. The cassette holder 4 is held in place by a support member 5 and slidably engages with a support column (not numbered). The x-ray beam passes through imaging area 11 to expose a film in the cassette. In a digital unit, the cassette tunnel openings are not present. X-ray beams used in conjunction with a digital bucky are received electronically. The solid area 8 is typically not transparent to x-ray beams and secures the cassette holder or bucky to the support column. A patient's breast (not numbered) is positioned on the imaging area 11 of the tube-side surface of the cassette holder 4 and is compressed by the compression device 3.

Figure 3:
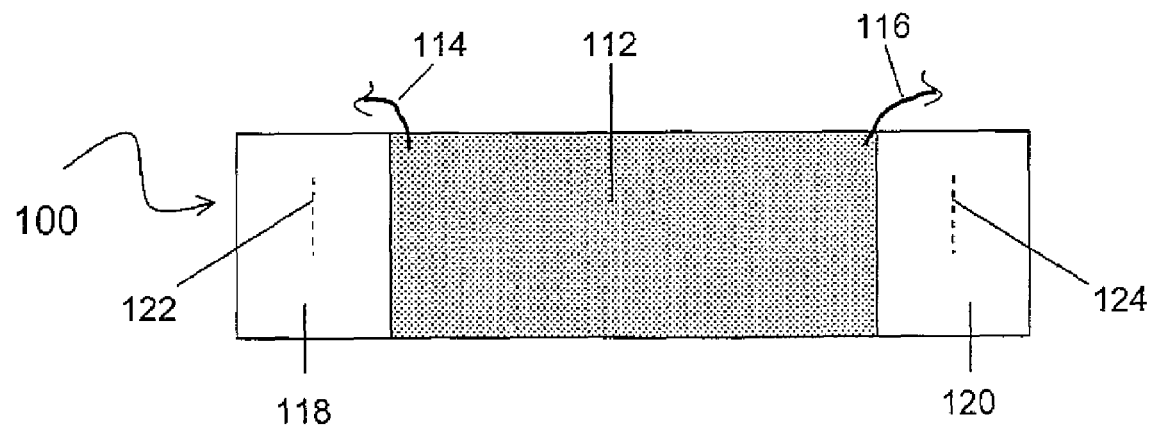
FIG. 3 is a schematic top view of an embodiment of the present invention.
Figure 4:
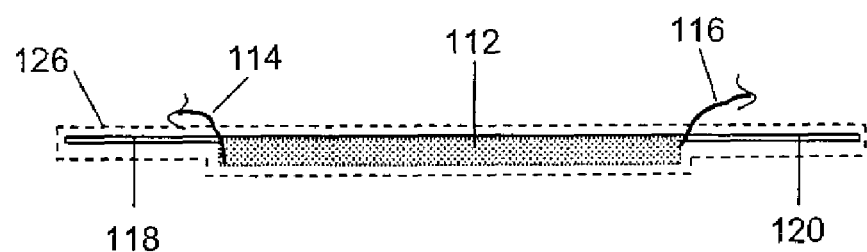
FIG. 4 is a schematic side-view of an embodiment of the present invention.

FIG. 3 is a schematic top view of an embodiment of the present invention. FIG. 4 is a schematic side-view of an embodiment of the present invention. An x-ray transparent inflatable chamber 112 has at least one manifold 114 that is operatively associated with the chamber 112, which can introduce compressed gas, for example, into the chamber and/or receive compressed gas to vent it from the chamber. A source of fluid, for example, compressed air, enters the chamber 112 of the device 100 through a manifold 114. An optional second manifold 116 can be operatively with the chamber for venting or fluid inlet purposes. The device 100 secures a patient's breast to a bucky by wrapping over the breast. In an embodiment, one or more flaps, 118 and 120, made of, for example, adhesive or elastic, attach to one or more ends of the chamber. The flaps optionally have one or more openings 122, 124 to permit a film cassette to pass through them into the cassette holder.

In some embodiments, an x-ray transparent cover 126 substantially surrounds the inflatable chamber. In some instances, it may be desirable that the x-ray transparent cover is compressible. In other instances, the x-ray transparent cover is disposable. A combination of compressible and disposable covers can also be used. For example, in one embodiment, a cuff made of compressible material can have a pocket for holding a high pressure balloon where the cuff wraps around and/or releasably adheres to the breast and the bucky.

In one embodiment, the inflatable chamber has multiple chambers. In one example, a chamber is nested within the cavity of another chamber. Another example is a combination of chambers next to each other. The use of multiple chambers can be used to help distribute the compression force exerted against the breast. The shape of the chambers can vary as needed too.

In evaluating equivocal areas of a mammogram it is sometimes desirable to provide a greater degree of compression in a localized area of a breast than can be achieved by uniform compression. This procedure, called spot compression, can be accomplished with the present invention by configuring at least one surface of the chamber with an area that expands to a greater degree than the surrounding surface, and positioning this area over the region of interest. Alternatively, an x-ray transparent semi-rigid plastic disc can be placed on the breast over the area of interest before overlaying the breast with the compression device. As air is introduced into the chamber, the disc is pushed against the breast to exert additional compression force in the localized area. The discs can vary in size as needed.

Figure 5:
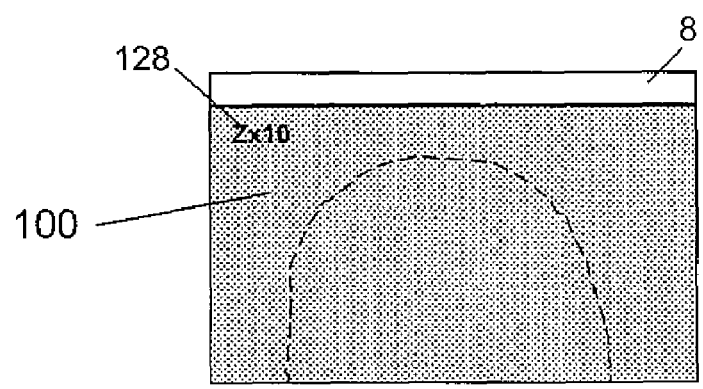
FIG. 5 is a top-view of an embodiment of the present invention.

Any portion of the devices can comprise radiopaque indicia. FIG. 5 is a top-view of a device 100 that wraps the tube-side area of a breast and contacts the surface of the bucky. Optionally, indicia 128 is contained on a surface of the device 100. Preferably, the indicia imparts information onto the mammogram in an area away from the breast.

Figure 6:
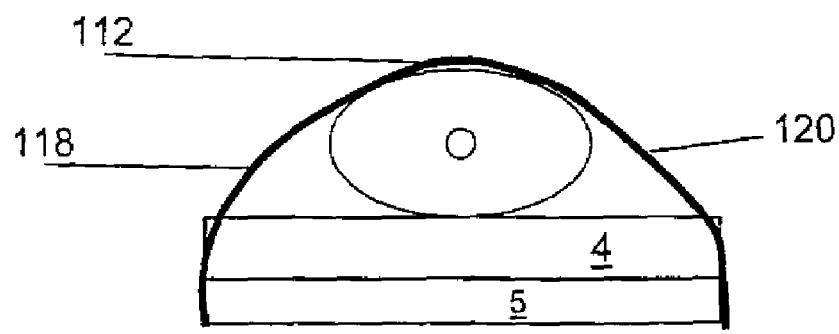
FIG. 6 depicts a side-view of an embodiment of the present invention.
Figure 7:
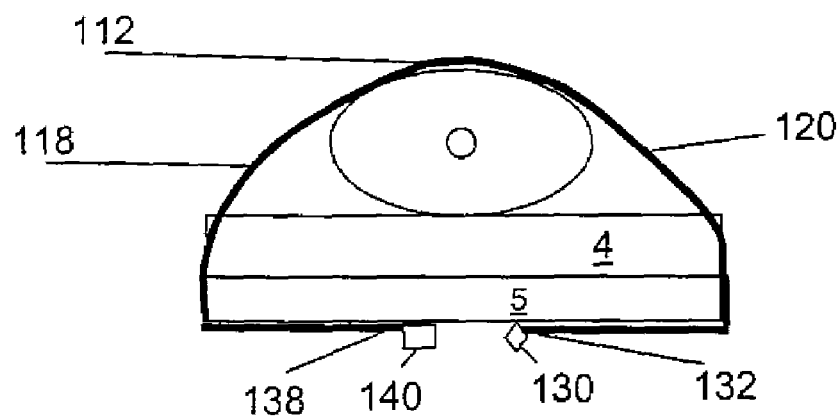
FIG. 7 depicts a side-view of an embodiment of the present invention.

In FIG. 6, depicting a side-view of an embodiment of device 100 in conjunction with a bucky 4, the device is positioned above a patient's breast in contact with the tube-side surface of the breast, referred to as such because this is the surface facing an x-ray tube of the mammography unit. In this embodiment, there are two side flaps 118 and 120 that secure the breast to the bucky 4 and attach to support member 5 (when a film-based bucky is being used). In FIG. 7, a free end of a first flap 130 can have a first fastener, 132. A second free end 138 can have a second fastener 140. The fasteners are optionally attachable or engagable with each other or individually to the bottom of the support member or bucky. In another example, a flap is secured, either permanently or removable, to a surface of the bucky. Generally, when in position over the breast (and not inflated) as shown in FIG. 6, the inflatable chamber 112 partially conforms to the shape of the breast. Compressed air, for example, can be introduced, manually or automatically, to inflate the chamber 112.

Figure 8:
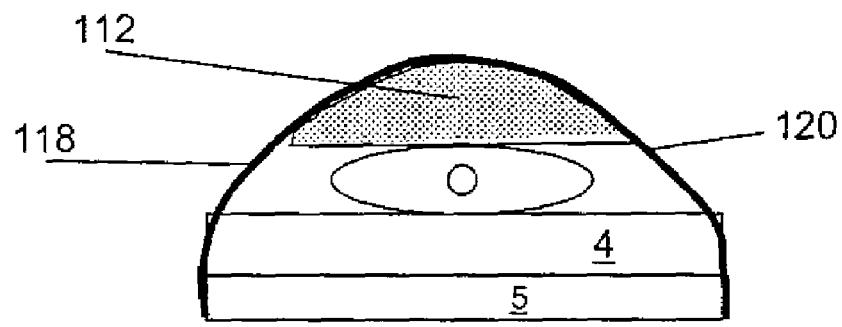
FIG. 8 depicts a side-view of an embodiment of the present invention.

As shown in FIG. 8, when fluid is introduced into the chamber 112, at least one surface of the chamber expands in the direction of the bucky 4. As the chamber expands, breast motion is limited and the breast is compressed against the bucky 4.

While the invention has been described and illustrated with reference to specific embodiments, those skilled in the art will recognize that modifications and variations may be made without departing from the principles of the invention as described herein and set forth in the following claims.

What is claimed:

1. A device for use with a bucky of a mammography unit for imaging a patient's breast comprising:
   at least one x-ray transparent inflatable chamber for containing a fluid;
   and wherein the device is secured to the side or bottom surfaces of the bucky such that the breast is positioned between the device and the bucky; and wherein when the fluid is introduced into the chamber, at least one surface of the chamber expands in the direction of the bucky, such that, as the chamber expands, the breast is compressed against the top surface of the bucky.

2. The device of claim 1 wherein the fluid comprises compressed air.

3. The device of claim 1 wherein when the device is in use, the device contacts a tube-side surface of the breast.

4. The device of claim 1 further comprising x-ray transparent material that substantially surrounds the at least one inflatable chamber.

5. The device of claim 1 further comprising a first flap.

6. The device of claim 5 wherein the first flap comprises an adhesive.

7. The device of claim 5 wherein the first flap comprises a first free end and a first fastener, and the device further comprising a second flap having a second free end and a second fastener that engages with the first fastener.

8. The device of claim 1 further comprising radiopaque indicia.

9. The device of claim 1 further comprising a second x-ray transparent inflatable chamber for containing a pressurized gas.

10. The device of claim 1 further comprising at least one opening to permit a film cassette to pass through.

11. The device of claim 1 wherein the fluid comprises a pressurized gas.

12. The device of claim 11 further comprising a manifold that is operatively associated with the at least one inflatable chamber for introducing the pressurized gas into the inflatable chamber and/or for receiving the pressurized gas from the inflatable chamber.

13. A mammography unit for imaging a patient's breast onto a mammogram comprising:
   a bucky comprising an imaging area; and
   a compression device comprising at least one x-ray transparent inflatable chamber and a manifold operatively associated with the inflatable chamber for introducing a fluid into the inflatable chamber and/or for receiving the fluid from the inflatable chamber;
   wherein when fluid is introduced into the at least one chamber of the compression device, at least one surface of the chamber expands in the direction of the bucky, such that, as the chamber expands, the breast is compressed against the top surface of the bucky; and
   wherein the device is secured to the side or bottom surfaces of the bucky such that the breast is positioned between the device and the bucky.

14. The mammography unit of claim 13 further comprising an x-ray transparent cover that substantially surrounds the inflatable chamber.

15. The mammography unit of claim 14 wherein the x-ray transparent cover is compressible.

16. The mammography unit of claim 14 wherein the x-ray transparent cover is disposable.

17. The mammography unit of claim 13 further comprising a source of compressed air in fluid communication with the manifold.

18. The mammography unit of claim 13 wherein the device further comprises radiopaque indicia which impart information onto the mammogram in an area away from the breast.

19. The mammography unit of claim 14 wherein the x-ray transparent cover further comprises radiopaque indicia which impart information onto the mammogram in an area away from the breast.

20. A method of imaging a patient's breast onto a mammogram comprising:
   securing a compression device comprising at least one inflatable chamber over a tube-side surface of the breast, wherein the device is secured to the side or bottom surfaces of a bucky such that the breast is positioned between the device and the bucky;
   inflating the at least one chamber of the compression device with a fluid;
   compressing the breast between the at least one inflatable chamber and an imaging area of the bucky;
   such that, as the chamber expands, the breast is compressed against the top surface of the bucky; and
   transmitting x-rays through the breast and onto the mammogram.

21. The method of claim 20 wherein the fluid comprises air, the method further comprising using a source of compressed air to inflate the at least one chamber of the compression device.

* * * * *